United States Patent
Ben-Arye et al.

(10) Patent No.: US 11,096,557 B2
(45) Date of Patent: Aug. 24, 2021

(54) ENDOSCOPY SYSTEM HAVING A MINIATURE CLOSED HEAD

(71) Applicant: EYELUM LTD., Zichron Yaakov (IL)

(72) Inventors: Asaf Ben-Arye, Zichron Yaakov (IL); Ofer Becker, Haifa (IL)

(73) Assignee: EYELUM LTD., Zichron Yaacov (IL)

( * ) Notice: Subject to any disclaimer, the term of this patent is extended or adjusted under 35 U.S.C. 154(b) by 96 days.

(21) Appl. No.: 16/081,955

(22) PCT Filed: Mar. 13, 2017

(86) PCT No.: PCT/IL2017/050320
§ 371 (c)(1),
(2) Date: Sep. 4, 2018

(87) PCT Pub. No.: WO2017/158597
PCT Pub. Date: Sep. 21, 2017

(65) Prior Publication Data
US 2020/0154980 A1    May 21, 2020

Related U.S. Application Data

(60) Provisional application No. 62/389,862, filed on Mar. 14, 2016.

(51) Int. Cl.
*A61B 1/015* (2006.01)
*A61B 1/06* (2006.01)
*A61B 1/00* (2006.01)

(52) U.S. Cl.
CPC ...... *A61B 1/00066* (2013.01); *A61B 1/00043* (2013.01); *A61B 1/015* (2013.01);
(Continued)

(58) Field of Classification Search
USPC ........................................................ 600/177
See application file for complete search history.

(56) References Cited

U.S. PATENT DOCUMENTS 6,181,369 B1 * 1/2001 Ooshima ............ A61B 1/00177
348/66
6,478,730 B1   11/2002 Bala et al.
(Continued)

FOREIGN PATENT DOCUMENTS

JP     2005124776 A   5/2005
WO  WO2012/060932 A2  5/2012

OTHER PUBLICATIONS

European Patent Office, Search Opinion in EP18853096.8, dated Apr. 28, 2021, p. 2 (physical p. 6)—the last 4 paragraphs of section 1.1.

*Primary Examiner* — John P Leubecker
(74) *Attorney, Agent, or Firm* — Alphapatent Associates, Ltd; Daniel J. Swirsky

(57) ABSTRACT

An endoscope assembly comprising a handle incorporating a liquid reservoir and injection system, a flexible or rigid cannula attaching to the handle, and a distally attached miniature imaging head. The imaging head is a transparent tubular shaped body having an essentially closed proximal end, and a tubular wall extending from the closed proximal end to the distal open end of the body. An optical source is attached to the closed proximal end, and its emitted illumination directed into the tubular wall of the body, such that said illumination is internally reflected within the tubular walls and is emitted from the distal open end. A detector array is disposed within the inner surfaces of the tubular wall section, and a lens images light reflected back into said imaging head, onto the detector array. The optical source is disposed radially inwards of the outer dimensions of the tubular shaped body.

15 Claims, 2 Drawing Sheets

(52) U.S. Cl.
CPC ......... *A61B 1/0607* (2013.01); *A61B 1/0684* (2013.01); *A61B 1/00096* (2013.01); *A61B 1/0676* (2013.01)

(56) References Cited

U.S. PATENT DOCUMENTS

| | | | |
|---|---|---|---|
| 6,863,651 B2 | 3/2005 | Remijan et al. | |
| 7,442,167 B2 * | 10/2008 | Dunki-Jacobs | A61B 1/0653 |
| | | | 600/129 |
| 7,530,946 B2 | 5/2009 | Hartwick et al. | |
| 7,942,814 B2 | 5/2011 | Remijan et al. | |
| 8,038,602 B2 | 10/2011 | Gill et al. | |
| 8,317,689 B1 | 11/2012 | Remijan et al. | |
| 8,708,896 B2 | 4/2014 | Vayser et al. | |
| 8,803,960 B2 | 8/2014 | Sonnenschein et al. | |
| 9,220,400 B2 | 12/2015 | Petersen et al. | |
| 9,370,295 B2 | 6/2016 | Kienzle et al. | |
| 9,717,398 B2 | 8/2017 | Irion et al. | |
| 2006/0004256 A1 * | 1/2006 | Gilad | A61B 1/041 |
| | | | 600/160 |
| 2006/0068360 A1 | 3/2006 | Boulais | |
| 2008/0208006 A1 * | 8/2008 | Farr | A61B 1/0684 |
| | | | 600/178 |
| 2010/0004506 A1 * | 1/2010 | Saadat | A61B 1/00082 |
| | | | 600/109 |
| 2012/0065469 A1 * | 3/2012 | Allyn | A61B 1/005 |
| | | | 600/109 |
| 2013/0046142 A1 | 2/2013 | Remijan et al. | |
| 2014/0031834 A1 | 1/2014 | Germain et al. | |
| 2014/0107496 A1 * | 4/2014 | Hellstrom | A61B 1/05 |
| | | | 600/478 |
| 2014/0221740 A1 | 8/2014 | Kawula et al. | |
| 2014/0235942 A1 * | 8/2014 | Hellstrom | A61B 1/0615 |
| | | | 600/104 |
| 2016/0089002 A1 * | 3/2016 | Burton | A61B 1/015 |
| | | | 600/154 |

\* cited by examiner

ENDOSCOPY SYSTEM HAVING A MINIATURE CLOSED HEAD

CROSS-REFERENCE TO RELATED APPLICATIONS

This application is a U.S. National Phase Application under 35 U.S.C. 371 of International Application No. PCT/IL2017/050320, which has an international filing date of Mar. 13, 2017, and which claims priority and benefit from U.S. Provisional Patent Application No. 62/389,862, filed Mar. 14, 2016, the contents and disclosure of which are incorporated herein by reference in their entirety.

FIELD OF THE INVENTION

The present invention is related to the field of endoscopy. In particular, it relates to miniature endoscopic devices, that combine an integrated liquid container and irrigation system, an imaging optical system with a head mounted LED source illuminating the field of view by means of a light guide.

BACKGROUND

Endoscopy is used for the inspection of internal organs, by means of insertion of visualization devices into the body through small incisions or through natural orifices. Typically, endoscopes are comprised of a camera and its associated optical system, a light source, as well as irrigation and working channel. Most flexible endoscopy devices also include a mechanical navigation component.

Small diameter endoscopes are used to penetrate into small anatomical cavities or thin tubal structures, such as in the nose and urinary system. Miniature endoscopes having a diameter in the range of 1.8 mm, or less, are required for inspection of organs with very small diameter lumens, such as the fallopian tubes, or to enhance the availability of visualization means, through minimally invasive incisions, sometimes no larger than a large needle insertion, such as for inspection of joints and small cavity organs. The use of such miniature endoscopes can enable performance of direct and immediate visualization of organs, in an office setting, thereby avoiding costly imaging methods, such as MRI or CT. An important requirement for enabling the availability of such devices to more clinicians is a small device having low manufacturing costs, which enables the entire endoscope to be disposable, if desired.

Most current endoscopy systems use LED illumination fiber optically transmitted from the proximal end, or from a LED mounted on the tip of the Endoscope. Such prior art illumination arrangements disadvantageously increase the diameter of the endoscope beyond the diameter dictated by the camera, camera housing, and optical imaging system. Some endoscopes have one or more illumination fibers or fiber bundles at or near the outer surface of the endoscope, and in order to provide enough illumination output, these fibers may be large, thereby increasing the total endoscope diameter. In U.S. Pat. No. 9,370,295, to R. A. Kienzle et al, for "Fully Integrated, Disposable Tissue Visualization Device", for example, there are multiple illumination fibers or fiber bundles surrounding the image guide, and the diameter is further increased by an infusion lumen and an outer tubular body. Other endoscope designs incorporate a light source at the proximal end of the endoscope and a sheath acting as a waveguide spanning the entire length of the endoscope such as is shown in U.S. Pat. No. 6,478,730 to J. L. Bala et al, for "Zoom Laparoscope". This sheath increases the diameter of the entire length of the endoscope beyond what is necessary to house the camera. Such a sheath may also involve additional absorption of light due to the length of transmission, which may reduce the usable illumination. In addition to increasing the diameter of endoscopes, sheath waveguides and fibers that run the entire length of the endoscope increase design complexity and construction costs, reducing disposability and maneuverability. Even in cases where there are no large fibers or sheaths, and only LEDs embedded in the camera housing at the distal end of the endoscope, such as in U.S. Pat. No. 9,220,400 to L. K. G. Peterson for "Endoscope having a Camera Housing and Method for making a Camera Housing", the LEDs are peripheral to the camera and thus increase the diameter of the endoscope.

Most endoscopes are also connected to a power-supply by an electrical cable, and receive their liquid supply for irrigation from an external irrigation source, such as from dedicated fluid bags, or by means of an external irrigation device. An external irrigation device as described in US 2006/0068360 to D. R. Boulais for "Single Use Fluid Reservoir for an Endoscope" requires a dedicated surface to rest upon and thus decreases maneuverability. It requires additional construction, increasing the cost of the endoscope, and requires a high pressure output to inject fluid, as the device is far from the area to be injected.

In particular, the diameter limitations of prior art endoscopes is problematic for many applications on small diameter lumens or small organs, and there therefore exists a need for a miniature, small diameter, simple construction disposable endoscope, which provides adequate light and fluid output while overcoming at least some of the disadvantages of prior art systems and methods.

A low cost, disposable endoscope, increases the availability of such a diagnostic modality to more physicians, enabling them to conduct endoscopic examinations in clinics, without the need to purchase and maintain costly endoscopic equipment, which typically including an electronic tower and a reusable endoscope requiring cleaning and sterilizing. In addition, low diameter endoscopes required for viewing small lumens, are hard to re-process, thus increasing the probability for contamination when re used.

The disclosures of any publications mentioned in this section and in other sections of the specification, are hereby incorporated by reference, each in its entirety.

SUMMARY

The present disclosure describes new exemplary systems for miniature endoscopes, having a simple construction, and a small outer diameter while still providing adequate imaging, light and fluid output. A particularly advantageous implementation uses a handle at the proximal end of the endoscope, a rigid or flexible cannula extending from the handle to the head, and an imaging head incorporating the illumination source at the distal end of the cannula. The term distal throughout this disclosure means the portion of the device which is closest to the patient or subject, and proximal is used to describe the portion of the device which is closest to the user, such as a doctor.

The imaging head contains at least one LED illumination source located in the proximal end of the endoscope head in such a position that it does not extend beyond the diameter determined by the diameter of the imager and its housing. The proximal end of the endoscope head may be completely or mostly closed, and may be tapered such that there is a reduction in the diameter as compared to the distal end of the endoscope head. Light is transferred from the illumination source to the distal end of the endoscope head using internal reflection along the walls of the lens holder, avoiding the need for long optical fibers and enabling a more maneuverable, low diameter and low cost endoscopy system. Positioning of this light source within the outer diameter of the lens holder in the endoscope head enables the maintenance of a diameter no larger than that of the imager. Penetration to small volume organs or lumens requires only a small volume of liquid irrigation, which therefore can be supplied by a small-integrated liquid reservoir and injection system located in the endoscope handle at the proximal end of the endoscope. The low construction cost, enables the entire endoscope device to be disposable, reducing risk of contamination to the patient.

Images from the camera may also be transmitted by means of a wireless connection link, to save the need for additional signal cables back to the home console, thereby providing more flexibility to the user and avoiding cumbersome maneuverability. However, the advantage of wireless connection may be offset by the added cost. The LED light source(s) can be powered by a battery, which can conveniently be located in the operator's handle of the device, and connected to the LED source either by wires or by printed conductors along the walls of the cannula shaft of the endoscope. For suitably miniaturized batteries, the batteries may be installed on board the endoscope head.

The size of the exemplary miniature endoscope system enables its entry into very small bodily lumens and requires only a minimal incision, which further reduces risks to the patient. Such a proposed device increases the availability of endoscopy means to more physicians, because it is affordable and enabled in the doctor's office with sterility ensured by one-time use of each disposable device, and low overhead costs.

An exemplary implementation of the endoscope uses an essentially transparent head incorporating a light transfer optical system for conveying illumination from the head mounted light source(s), typically a low cost LED, to the exit aperture for illuminating the field of view. The light transfer system is based on the use of the tubular wall of the endoscope head, and particularly the lens holder part of the endoscope head, as a light guide, with internal reflection being used to convey the illumination from the LED source (s) down the reflective tubular wall to the exit aperture. The exit aperture and tubular form of the endoscope head may be any suitable shape, such as circular (annular) or elliptical.

The optical imaging system should include a miniature imaging sensor integrated into the endoscope head, located distally to the light source. The endoscope head should also contain one or more imaging lenses located distally to the imaging sensor. The light is generated by one or more LEDs, located at the proximal end of the head, and is directed internally along the tubular wall of the head, which also functions as the lens holder barrel. The angle at which the light is directed from the LED(s) towards the tubular wall may be chosen to be greater than the critical angle with respect to the normal to the tubular wall surface, and thus one which will result in internal reflection. The wall of the head is made of light transferring material, with reflective inner and outer surfaces to confine the light to propagate within the material of the head. Such a reflective surface may readily be obtained by using a reflective outer coating with an adequate refractive index so as, in combination with a sufficiently large angle of emitted light, to allow internal reflection according to Snell's law, or alternatively though possibly less effectively, by relying on the total internal reflection properties of the transparent material in the air and fluid medium surrounding it. Using the walls of the device for transferring the light from the proximal end of the head to the distal output aperture, reduces the endoscope diameter, because it eliminates the prior art need for an additional light transfer element, such as an optical fiber, or the use of LED(s) placed peripherally to the optical system, thus consuming space and increasing the diameter of the endoscope beyond that dictated by the camera. Integration of the light source into the diameter of the endoscope head by placing the LED(s) behind the camera and by means of using the wall of the endoscope head, or part of it, as a light-guide, reduces the overall diameter of the endoscope head, which is generally the part of the endoscope with the largest diameter.

The one or more light sources may advantageously be white light source(s), such as white emitting LED(s). However, blue LEDs can be used as the illumination source, by utilizing a phosphor at the distal end of the light transfer unit, which will then convert the blue wavelength to white light. The use of such a configuration allows the use of blue LEDs, with higher lumens/area density, thereby improving costs, and the decreasing overall heat dissipation of the module. In addition, the light uniformity on the image may be improved, contributing to the image quality.

Endoscopy devices need irrigation means to help open their path along the investigated organ or lumen, and to clean that region to be viewed. This irrigation is generally performed in the prior art by external connection from a liquid reservoir, through a tube or set of tubes into the endoscope, creating a cumbersome structure that may limit operator/ surgeon flexibility during the procedure. In contrast, the small diameter devices described in the present disclosure for insertion into small volume organs, need a lower volume of liquid, and thus can use a relatively small liquid reservoir. In the presently described endoscopes, such a compact reservoir is sufficiently small that it can be contained in the volume of the handle. A reservoir that is within the handle and not external to the whole endoscope device may be closer to the distal end of the endoscope, and thus require a lower pressure input to cause the liquid to flow from the reservoir to the region to be cleaned. Such an integrated reservoir enhances the disposability of the entire endoscope device.

Furthermore, the handle may contain an integrated injection mechanism, either hand operated by the user, though optionally electrically powered, injecting liquid from the reservoir along the flexible cannula of the endoscope towards the distal end of the device, where it is discharged into the organ or lumen through an irrigating opening(s). Such a function is effective for the small diameter endoscopes described in the present disclosure, because of the small quantities of fluid required.

In addition to the irrigation liquid container, the liquid injection mechanism, and the battery and circuitry that provides power to the electronic components of the device, the handle may also contain a wireless transmitter unit for transferring images and data acquired by the imaging system back to a display console, such as a computer screen, a mobile phone or any other designated display.

The combination of an integrated liquid reservoir, an injection mechanism, wireless image transmission and an integrated battery based power supply enable higher maneuverability and flexibility to the user, because there is no need to connect any wires or tubes to an endoscope control console, or to any services provided externally to the endoscope.

Furthermore, such an assembly enables lower production cost, thus increasing the availability of the device for various applications and medical procedures, such as for Falloposcopy, Ear Nose and Throat applications, Arthroscopy, urology and other minimally invasive surgical procedures.

The miniature endoscopes described in the present disclosure can be used for penetration and visualization of tubal anatomical organs or small cavities or for penetration through very small, needle-size incisions. Once through the skin or penetrated into its target organ, small liquid injection maneuvers can enhance forward movement of the endoscope tip and can open collapsed tubes, as well as help cleaning the region in front of the camera. Although the endoscope cannula is shown as a flexible tube in the drawings of this application, thus enabling maneuvering through curving lumens and into locations behind other organs, the endoscope can also be implemented using a rigid shaft connecting the handle with the endoscope imaging head, and this disclosure is intended to apply to such a rigid tube endoscope implementation also.

There is thus provided in accordance with an exemplary implementation of the devices described in this disclosure, an endoscope for insertion into a subject an endoscope for insertion into a subject, comprising:
(i) a handle comprising a liquid reservoir and a liquid injection system,
(ii) a cannula attached at its proximal end to the handle, the cannula having at least one opening through which liquid from the reservoir can be ejected, and
(iii) an imaging head attached to the distal end of the cannula, the imaging head comprising:
(a) a transparent tubular shaped body having (i) an essentially closed proximal end, and (ii) a tubular wall extending from the closed proximal end and terminating at a distal open end of the tubular shaped body,
(b) at least one light source associated with the essentially closed proximal end, and positioned such that its emitted illumination is directed into the tubular wall of the transparent tubular shaped body, is internally reflected within the tubular wall and is emitted distally therefrom,
(c) a two dimensional detector array disposed within the inner surfaces of the tubular walls, and
(d) at least one imaging lens positioned distally to the detector array, such that it images onto the detector array, light reflected back into the imaging head,
wherein the at least one optical source is disposed radially inwards of the outer dimensions of the tubular shaped body.

In such an endoscope, the illumination may be internally reflected within the tubular walls by total internal reflection. Alternatively, at least parts of the inner and outer surfaces of the tubular wall have optically reflective coatings such that the illumination is internally reflected within the tubular walls. The closed proximal end may be curved, conical or coated with a phosphorescent material. Additionally, the distal end wall of the tubular wall may be flat, curved or tilted.

In any of the above described endoscopes, the detector array may be disposed with its optically sensitive face directed at the open end of the tubular shaped body, and at a distance from the at least one lens essentially equal to the effective focal length of the at least one lens. Alternatively, it may be disposed off-axis, with its surface aligned along the tubular shaped body, the image head further comprising a bending mirror surface to direct light collected by the at least one lens onto the detector array.

The endoscope may also comprise a battery for powering the at least one optical source, the battery being disposed in the handle. The handle may also comprise a wireless transmitter for transmitting to a user console images received images from the detector array. Furthermore, the at least one optical source may comprises at least one light emitting diode. In further implantations, the tubular wall may be the barrel of the at least one imaging lens.

According to yet further proposed implementations, in any of the above-mentioned endoscopes the distal one of the at least one imaging lens is designed such that its distal surface is convex shaped such that it reduces trauma to the anatomical site through which the endoscope is passed. In addition, the imaging head may be less than 1.7 mm. in diameter and 5 mm. in length. Finally, the cannula may comprise an electroactive polymer material.

BRIEF DESCRIPTION OF THE DRAWINGS

The present invention will be understood and appreciated more fully from the following detailed description, taken in conjunction with the drawings in which.

DETAILED DESCRIPTION

Figure 1:
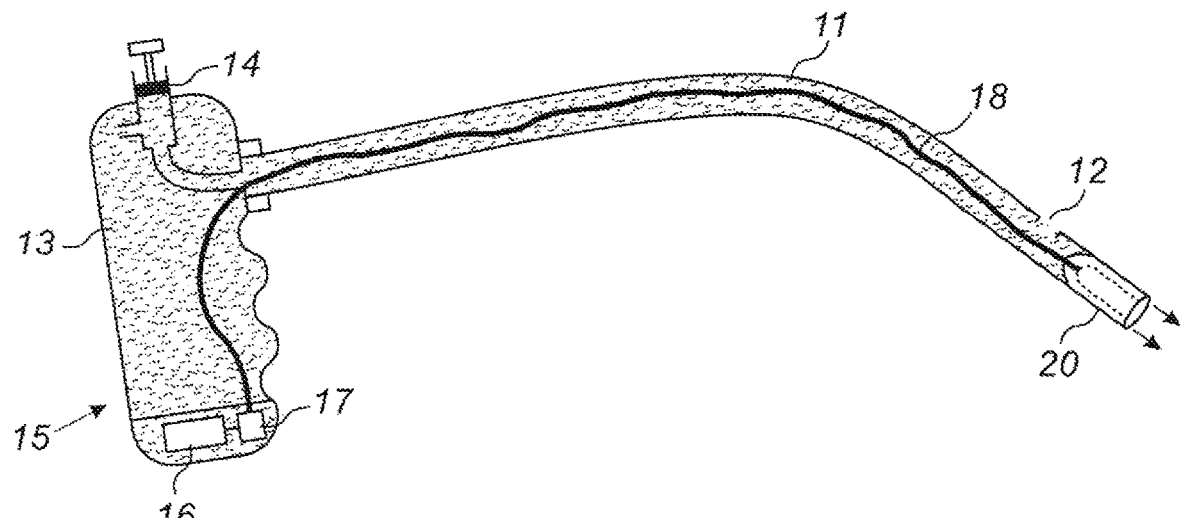
FIG. 1 illustrates schematically an exemplary miniature endoscope system according to one implementation of the present disclosure.
Figure 2A:
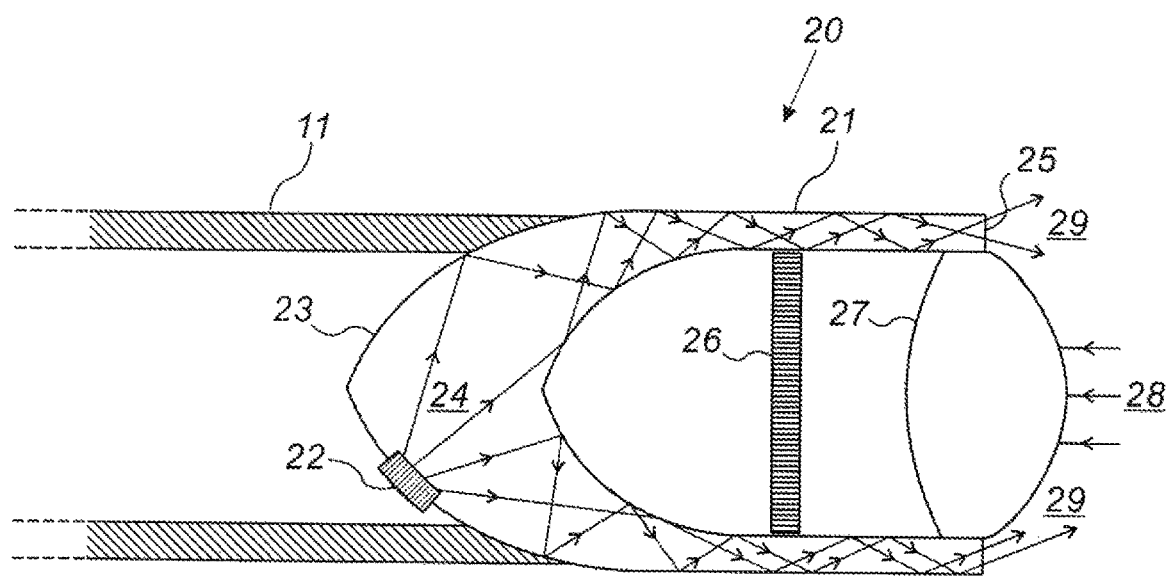
FIGS. 2A to 2C are schematic representations of cutaway sections of three different embodiments of the endoscope head, showing the internal optical illumination and imaging system.

Reference is now made to FIG. 1, which illustrates schematically an exemplary endoscope system according to one implementation of the present disclosure, which can provide a small diameter, low-cost system. The endoscope head 20 is disposed on the end of a catheter shaft 11, which can be stiff or flexible. The head is shown in the form of an essentially cylindrical or tubular extremity having a diameter or maximum outer dimension, which need be no larger or not substantially larger than that of the catheter shaft. The internal construction of the endoscope head is shown in FIG. 2A, hereinbelow. The catheter shaft 11 may have one or more openings 12 along its length, especially near the distal end, for injecting irrigation fluid into the lumen or organ being inspected. Because the endoscope is intended for use in small size lumens or within small volume organs, the amount of irrigation fluid required is small, and in the implementation shown in FIG. 1, may be supplied by a liquid reservoir 13 such as a plastic container, with an injection mechanism 14 such as a manually operated plunger or a bellows or a balloon, for forcing the irrigation fluid out of the catheter shaft. This irrigation system can thus be self-contained by installation in the handle 15 of the endoscope system. The battery 16 and any associated electronic circuitry 17 for powering the light source, the imager, and possibly also the irrigation mechanism and the wireless data transmission apparatus in the endoscope head, as to be shown in FIG. 2A, may also conveniently be installed in the endoscope handle 15, and the current transferred by lead 18 to the endoscope head 20. The injection mechanism may optionally be actuated electrically, such as from the installed battery, or from an external power source.

In the implementation shown in FIG. 1, the endoscope head 20 is connected by means of electrical wires 18 to the handle mounted battery 16. Alternatively, if the battery is small enough, it may be positioned within the head (this implementation not shown in FIGS. 1 to 3). Signals from a head mounted camera sensor, may optionally be transferred to a wireless transmitter unit (not shown) by means of a wire connecting the camera to the wireless transmitter unit.

Reference is now made to FIG. 2A, which illustrates schematically a cutaway cross-section of an exemplary endoscope head 20 showing the component optical parts of the head, encompassing its illumination and imaging system. The endoscope head is constructed of a transparent material, such as a clear plastic or glass-like material. The head 20 may be conveniently shaped like a tube having a rounded closed proximal end with an elliptic or parabolic or circular cross section, and with the tube walls 21 leading to the open distal end of the endoscope head. One or more light sources such as LED devices 22, are attached or embedded into the surface of the base 23 of the endoscope head, preferably by optical bonding, such that they emit their illumination into the transparent material of the curved base of the head, in a generally distal direction. Alternatively, the endoscope head can be formed by molding, with the illuminating devices fixed in position in the molded body. A number of emitted rays of illumination 24 are shown in FIG. 2A. The LED or LEDs have to be attached to or recessed into the curved or flat shaped section of the outer and proximal closed end of the cylinder, since in that position, they do not jut out beyond the diameter of the cylindrical housing, and therefore do not increase the overall outer diameter of the endoscope head. The inner surface of the closed tubular end of the endoscope head is also shown to be curved, typically in an ellipsoidal or paraboidal or spherical form. This base and the distal walls of the closed cylindrical head, enclose the internal volume of the head, which generally contains air. Selected surfaces or all of the surfaces of the light guide or cylinder walls, both internal and external surfaces, could be coated with a reflective coating, so that illumination 24 impinging on the transparent solid/air interface is internally reflected in a distal direction down the walls of the cylindrical tube, until the illumination is emitted 29 from the distal annular end wall 25 to illuminate the field of view in front of the endo scope head. This distal annular end wall 25 is shown flat in FIG. 2A, but could also be curved or tilted.

The position of the LED source 22 or sources, and the structure of the internal base surface of the endoscope head are shaped so as to ensure that the majority or all of the incident illumination on the solid/air interface is internally reflected and does not pass out of the cylindrical wall into the inner volume of the endoscope head, or out of the outer wall of the body. The cylinder wall thus acts as a light waveguide from the source or sources 22 to the annular emitting aperture 25. It is to be understood that although the endoscope body is described in this implementation as being cylindrical or tubular, usually understood to having a circular cross section, this being the most cost-effective and convenient form to use, the invention is not intended to be limited to a pure right circular cylindrical shape, but that any other suitable shape, such an oval or elliptical shaped cylinder, could also be used. The term cylinder, and derivatives, such as cylindrical, or tubular, as recited and as claimed in this application, are not therefore intended to be limited to having circular cross sections, but can be understood to have other suitable cross sections also.

An imaging sensor 26, such as a CMOS detector array, is disposed inside the central volume of the endoscope head near the proximal end, with at least one imaging lens 27 disposed distally of the sensor array 26, such that illumination 28 reflected from parts of the imaged organ or lumen, not shown, within the field of view of the emitted illumination 29 is focused by the imaging lens 27 onto the sensor array 26. The imaging system thus provides an image of the region distally in front of the endoscope head, having high image quality and good visualization of the examined organ. The imaging lens 27 may advantageously be located at the tip of the cylinder at the very proximal end of the endoscope head. The lens design provides an atraumatic distal end, having a curved shaped structure that avoids damage to anatomical structures that come into engagement with it during a procedure. Furthermore, the transparent material of the endoscope head may be selected to have a certain limited level of flexibility, such that if the head encounters an obstruction in the lumen into which it is being inserted, it will deform slightly rather than undergoing breakage, which could be damaging to the patient. However the level of flexibility must be such that the mutual position of the lenses and the imaging sensor are not moved to such an extent that the image quality is degraded.

The endoscope head 20, is attached to the distal end of the catheter shaft 11 such that it can be maneuvered within the patient's body to the site to be inspected. The arrangement whereby the light source is contained within the diameter of the sensing element enables a substantial reduction in head diameter to be achieved. The size of the head currently produced is 1.7 mm. in diameter by 5 mm in length, but even smaller head units can be envisaged as the size of the imaging arrays becomes smaller.

Figure 2B:
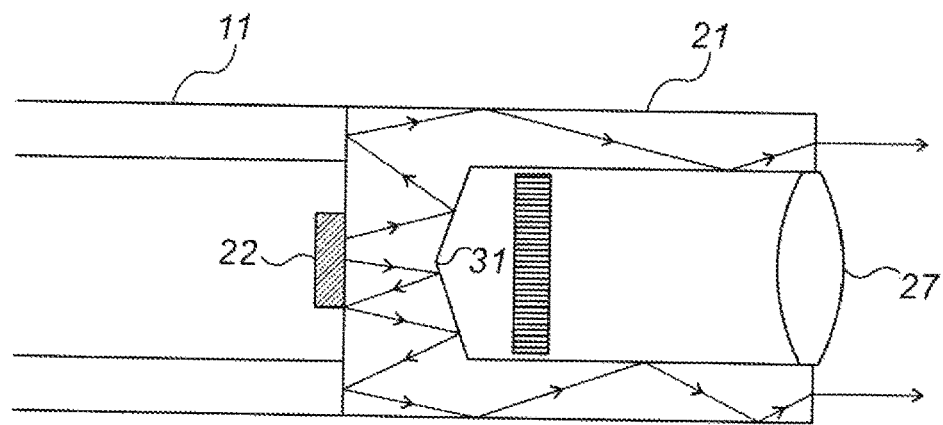

Reference is now made to FIG. 2B, which illustrates schematically an alternative arrangement for the mounting of the illumination source or sources in the head, using a flat-backed 30 housing cavity, to simplify the mounting. The dispersion of the illumination from the LED chip 22, and a reflective coating 31 to the cone shaped back surface of the cavity ensures that the illumination does remain within the transparent body material and is directed to the tubular output walls 21.

Figure 2C:
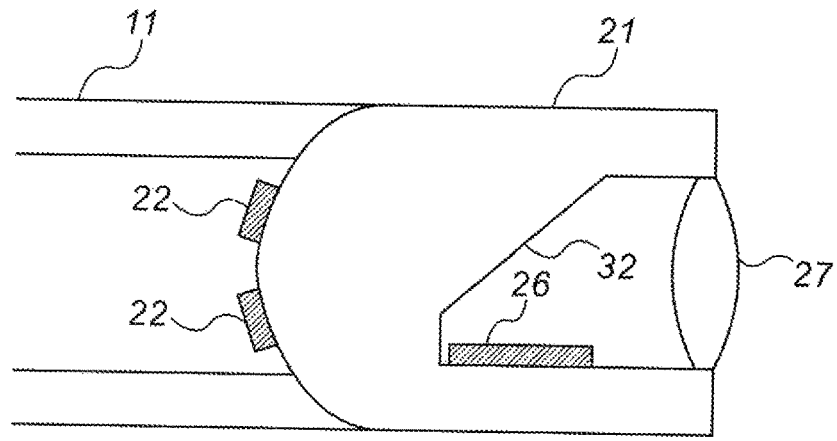

Reference is now made to FIG. 2C, which illustrates schematically an alternative position for mounting the detector array 26, using a beam-bending surface 32. By using the length of the head cavity to locate the detector array, this implementation may enable the use of a larger detector array having a larger number of pixels for increased image resolution. The beam-bending mirror surface can conveniently be formed as a 45° aligned base wall 32 of the internal cavity of the head, with the mirror property defined by means of an internal coating.

The layouts of the arrangements of FIGS. 2B and 2C are being brought as examples of alternative implementations of the arrangement of FIG. 2A, and are not intended to be exhaustive. The inventive aspect of all of these implementations is that the head of the endoscope is designed to enable the illumination to be emitted from the distal end without the illumination source essentially protruding beyond the outer dimension of the head, as determined by the maximum size of optical component installed therein.

Figure 3:
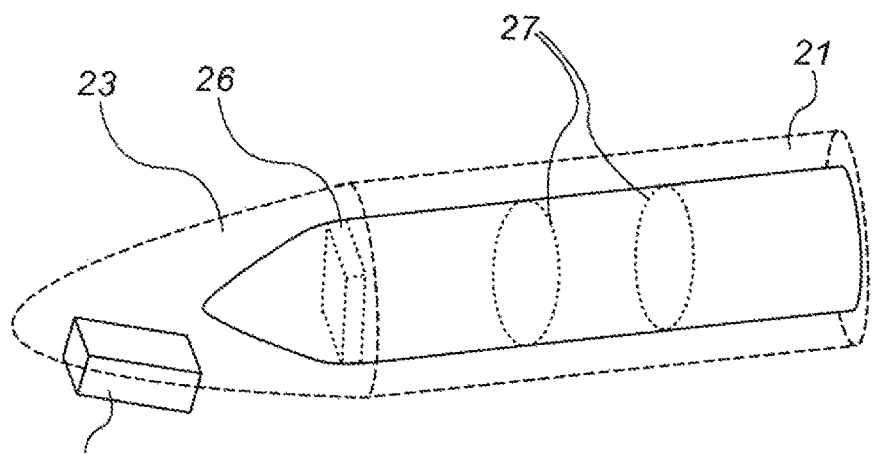
FIG. 3 is an isometric view of an exemplary endoscope head such as that of FIG. 2A.

Reference is now made to FIG. 3, which is an isometric view of an exemplary endoscope head, showing the transparent body 23, a LED illumination source 22, an imaging sensor 26 and a typical pair of imaging lenses 27 mounted within the transparent barrel 21, and their mutual positions within the head.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. An endoscope for insertion into a subject, comprising:
   a handle comprising a liquid reservoir and a liquid injection system;
   a cannula attached at its proximal end to said handle, said cannula having at least one opening through which liquid from said reservoir can be ejected; and
   an imaging head attached to the distal end of said cannula, said imaging head comprising:
      a transparent tubular shaped body having (i) a closed proximal end, and (ii) a tubular wall having inner and outer surfaces extending from its closed proximal end and terminating at a distal end of said tubular shaped body;
      at least one light source associated with said closed proximal end, disposed inwards of the radius of the outer surface of said tubular shaped body, and positioned such that its emitted illumination is directed into the tubular wall of the transparent tubular shaped body, is internally reflected within said tubular wall and is emitted distally therefrom;
      a two dimensional detector array disposed within the inner surface of said tubular wall; and
      at least one imaging lens positioned distally to said detector array, such that it images onto said detector array, light reflected back into said imaging head,
   wherein said at least one imaging lens is mounted directly in said transparent tubular shaped body such that a closed internal volume is formed in said transparent tubular shaped body.

2. An endoscope according to claim 1, wherein said illumination is internally reflected within said tubular wall by total internal reflection.

3. An endoscope according to claim 1, wherein at least parts of the inner and outer surfaces of said tubular wall have optically reflective coatings such that said illumination is internally reflected within said tubular wall.

4. An endoscope according to claim 1, wherein said closed proximal end is curved.

5. An endoscope according to claim 1, wherein said closed proximal end is flat.

6. An endoscope according to claim 1, wherein said closed proximal end is conical.

7. An endoscope according to claim 1, wherein the distal end of said tubular wall is coated with a phosphorescent material.

8. An endoscope according to claim 1, wherein said detector array is disposed with its optically sensitive face directed at said distal end of said tubular shaped body, and at a distance from said at least one lens essentially equal to the effective focal length of said at least one lens.

9. An endoscope according to claim 1, wherein said detector array is disposed off-axis, with its surface aligned along said tubular shaped body, said imaging head further comprising a bending mirror surface to direct light collected by said at least one lens onto said detector array.

10. An endoscope according to claim 1, further comprising a battery for powering said at least one optical source, said battery being disposed in said handle.

11. An endoscope according to claim 1, wherein said at least one light source comprises at least one light emitting diode.

12. An endoscope according to claim 1, wherein said tubular wall is a barrel for said at least one imaging lens.

13. An endoscope according to claim 1, wherein a distal one of said at least one imaging lens is designed such that its distal surface is convex shaped such that it reduces trauma to the anatomical site through which said endoscope is passed.

14. An endoscope according to claim 1, wherein said cannula comprises an electroactive polymer material.

15. An endoscope according to claim 1, wherein said imaging head is less than 1.7 mm. in diameter and 5 mm. in length.

* * * * *